United States Patent [19]

Pâques

[11] Patent Number: 4,818,690
[45] Date of Patent: Apr. 4, 1989

[54] METHOD FOR THE DETERMINATION OF PLASMINOGEN ACTIVATORS (PA)

[75] Inventor: Eric P. Pâques, Marburg, Fed. Rep. of Germany

[73] Assignee: Behringwerke Aktiengesellschaft, Fed. Rep. of Germany

[21] Appl. No.: 849,717

[22] Filed: Apr. 9, 1986

[30] Foreign Application Priority Data

Apr. 11, 1985 [DE] Fed. Rep. of Germany ........ 3512909

[51] Int. Cl.$^4$ .......................... C12Q 1/56; G01N 33/86
[52] U.S. Cl. ........................................... 435/13; 435/4; 436/69
[58] Field of Search ............................. 435/13; 436/69

[56] References Cited

U.S. PATENT DOCUMENTS

| 4,011,142 | 3/1977 | Jacobi | 435/13 |
| 4,033,824 | 7/1977 | Karges et al. | 435/13 |
| 4,605,614 | 8/1986 | Nagasawa et al. | 435/13 |

OTHER PUBLICATIONS

Markwardt et al.—Chem. Abst., vol. 89 (1978), p. 36482k.
Ranby, "Studies on the Kinetics of Plasminogen Activation by Tissue Plasminogen Activator," Biochimica et Biophysica Acta, 704:461–469 (1982).
Patricia Andrade-Gordon and Sidney Strickland, Biochemistry 25:4033–4040, 1986.
E.-P. Paques, H.-A. Stohr, N. Heimburger, Thrombosis Research 42:797–807, 1986.

*Primary Examiner*—Sam Rosen
*Attorney, Agent, or Firm*—Finnegan, Henderson, Farabow, Garrett & Dunner

[57] ABSTRACT

A method for the determination of urokinase (UK) or tissue plasminogen activator (t-PA) is described, in which the activator is incubated with plasminogen, with a polysulfuric ester of a saccharide or with a sulfated sugar and, where appropriate, fibrin or fibrin degradation products, and the conversion of plasminogen into plasmin is determined, and agents suitable for this method are described.

11 Claims, No Drawings

METHOD FOR THE DETERMINATION OF PLASMINOGEN ACTIVATORS (PA)

The invention relates to a method for the determination of plasminogen activators (PA). The term plasminogen activator is intended to mean urokinase (UK) and tissue plasminogen activator (t-PA).

Plasminogen is converted into plasmin by plasminogen activators. The catalysts of this reaction include streptokinase, urokinase and t-PA. The detection of PA in samples of body fluid from patients is of particular significance for the early diagnosis of patients at risk of thrombosis. Methods of determination are known for measurement of the PA activity. However, owing to the low PA activity in body fluids, these require very long incubation. To increase the rate of activity, t-PA can be stimulated by addition of fibrin or fibrin degradation products (Biochim. Biophys. Acta (1982) 704, 461-469). A method for the determination of t-PA in the presence of fibrin is described in European Pat. No. 0,094,720. The preparation of fibrin or fibrin degradation products is elaborate, and the use of fibrin or fibrin degradation products is also limited by the low solubility of these components.

The present invention has the object of developing a method of detection of PA which is more sensitive, more rapid and more straightforward than those already known.

It has been found, surprisingly, that the activity of PA is considerably increased in the presence of polysulfuric esters of saccharides.

It has also been found, surprisingly, that polysulfuric esters of saccharides or sulfated sugars can replace or supplement the stimulating effect of fibrin or of fibrin degradation products on the t-PA activity in an assay system containing t-PA and plasminogen.

The invention relates to a method for the determination of a plasminogen activator (PA) in a body fluid, which comprises this PA being incubated with plasminogen and a polysulfuric ester of a saccharide or with a sulfated sugar or cell membrane constituents and, where appropriate, with fibrin or fibrin degradation products, and the conversion of plasminogen into plasmin being determined.

An example of an appropriate body fluid is plasma.

A chromogenic substrate is preferably used for determination of the conversion of plasminogen into plasmin.

The polysulfuric esters of saccharides or the sulfated sugars which can be used are, in particular, heparin, heparin sulfate, pentosan sulfate, dextran sulfate, keratan sulfate, chondroitin sulfate, dermatan sulfate or Arteparon ® (mucopolysaccharide polysulfate).

The polysulfuric esters are preferably used in a concentration of $10^{-8}$ to 1 mg/ml of assay mixture. Heparin is preferably used in a concentration of $10^{-5}$ to 1 mg/ml of assay mixture.

In a particularly preferred embodiment, the procedure for the determination of the PA activity can be such that 0.1 ml of a PA-containing sample is incubated at a temperature of 10°-40° C., preferably 30°-40° C., with 0.1 ml of a plasminogen solution containing 0.1 to 10, preferably 0.5-2, CTA/ml (Committee on Thrombolytic Agents), 0.1 ml of a solution containing $10^{-7}$ to 10 mg/ml, preferably $10^{-5}$ to 10 mg/ml, of a polysulfuric ester of a saccharide or sulfated sugar, preferably heparin in a concentration of $10^{-5}$ to 10 mg/ml, preferably $10^{-4}$ to 10 mg/ml, 0.7 ml of a buffer, preferably 0.1 mol/l tris.HCl, pH 6.5-8.5, where appropriate containing 0.1 ml/100 ml Tween ®80, and a plasmin-specific chromogenic substrate, for example HD-Phe-Tyr-Arg-ANBA ethyl ester, HD-Phe-Tyr-Lys-ANBA-neopentylamide or HD-Val-Leu-Lys-pNA, and the amount of the liberated chromophore is determined.

It has also been found, surprisingly, that cell membrane constituents can also stimulate PA activity.

In another particularly preferred embodiment, the procedure for the determination of the PA activity can be such that 0.1 ml of a PA-containing sample, for example plasma, is incubated, at a temperature 10°-40° C., preferably 30°-40° C., with 0.1 ml of a plasminogen solution containing 0.1 to 10 CTA/ml, preferably 0.5-2 CTA/ml, 0.1 ml of a solution containing lyzed cells, preferably platelets, preferably in a concentration of 25,000 to 2,500,000 cells/ml, or Staphylococci, preferably in a concentration of $10^{-4}$ to $10^{-1}$ g/ml, 0.7 ml of a buffer, preferably 0.1 mol/l tris.HCl, pH 6.5-8.5, where appropriate containing 0.1 ml/100 ml Tween ®80, and a plasmin-specific chromogenic substrate, for example HD-Phe-Tyr-Arg-ANBA ethyl ester, HD-Phe-Tyr-Lys-ANBA-neopentylamide or HD-Val-Leu-Lys-pNA, and the amount of the liberated chromophore is determined.

A calibration curve can be used for the evaluation. In the determination of t-PA activity, it is possible to add to the reaction mixture fibrin or fibrin degradation products, depending on the proportion of peptides stimulating plasminogen activator, in a concentration of 0.001 to 1 mg/ml in the assay mixture.

The method of determination of PA which has been described is particularly distinguished by the stimulation of PA, and thus there is an increase in the rate of activation of plasminogen and, consequently, the sensitivity is increased.

The invention also relates to an agent for the determination of a plasminogen activator, which contains at least 0.01 to 1 CTA/ml plasminogen and $10^{-4}$ to 1 mg/ml heparin and, where appropriate, 0.01 to 0.1 ml/100 ml polyoxyethylene sorbitan monooleate and, where appropriate, fibrin degradation products, to an agent of this type which contains at least 0.01 to 1 CTA/ml plasminogen and $2.5 \times 10^3$ to $2.5 \times 10^5$ platelets/ml and, where appropriate, 0.01 to 0.1 ml/100 ml polyoxyethylene sorbitan monooleate and, where appropriate, fibrin degradation products, and to an agent of this type which contains at least 0.01 to 1 CTA/ml plasminogen and $10^{-1}$ to 10 mg of Staphylococci/ml and, where appropriate, 0.01 to 0.1/100 ml polyoxyethylene sorbitan monooleate and, where appropriate, fibrin degradation products.

The invention is to be illustrated in detail by the examples which follow.

EXAMPLE 1

The assay mixture was composed of 0.1 ml of a t-PA-containing sample, 0.1 ml of plasminogen solution (1 CTA/ml), 0.7 ml of a buffer containing 0.1 mol/l tris.HCl, pH 7.5, and 0.1 ml/100 ml Tween ®80, and of the plasmin substrate HD-Phe-Leu-Lys-pNA (Kabi, Sweden) and, in addition, 0.1 ml of a heparin solution of various concentrations. The mixture was incubated at 37° C. for 20 min, and then the dyestuff development was stopped and the $OD_{405\ nm}$ was measured.

Table 1 shows the result.

TABLE 1

| Concentrations of heparin added (USP/ml assay mixture) | $OD_{405\,nm}$ | Stimulation factor |
|---|---|---|
| 0 | 0.082 | 1.00 |
| 0.005 | 0.103 | 1.26 |
| 0.05 | 0.406 | 4.95 |
| 0.5 | 0.941 | 11.48 |
| 5 | 0.594 | 7.23 |
| 50 | 0.097 | 1.18 |

USP = United States Pharmacopeia

EXAMPLE 2

As in Example 1, 0.1 ml of a platelet-containing solution of various concentrations being added in place of the heparin solution.
Table 2 shows the result.

TABLE 2

| Concentrations of platelets added (cells/ml assay mixture) | $OD_{405\,nm}$ | Stimulation factor |
|---|---|---|
| 0 | 0.082 | 1.00 |
| 2.5 | 0.109 | 1.33 |
| 25 | 0.116 | 1.42 |
| 250 | 0.190 | 2.32 |
| 2500 | 0.938 | 11.44 |
| 50000 | >3.000 | >36.59 |
| 250000 | 2.126 | 25.93 |

EXAMPLE 3

As in Example 1, 0.1 ml of a solution of lyzed Staphylococci of various concentrations being added in place of the heparin solution.
Table 3 shows the result.

TABLE 3

| Concentrations of Staphylococci added (mg Staphylococci/ml assay mixture) | $OD_{405\,nm}$ | Stimulation factor |
|---|---|---|
| 0 | 0.082 | 1.00 |
| $10^{-4}$ | 0.116 | 1.42 |
| $10^{-3}$ | 0.200 | 2.44 |
| $10^{-2}$ | 0.140 | 1.71 |
| $10^{-1}$ | 1.468 | 17.90 |
| 1 | >3.000 | >36.59 |
| 10 | 2.460 | 30 |

EXAMPLE 4

As in Example 1 with a UK-containing solution.
Table 4 shows the result.

TABLE 4

| Concentrations of heparin added (USP/ml assay mixture) | $OD_{405\,nm}$ | Stimulation factor |
|---|---|---|
| 0 | 0.151 | 1.00 |
| 0.005 | 0.420 | 2.78 |
| 0.05 | 0.676 | 4.48 |
| 0.5 | 0.971 | 6.43 |
| 5 | 0.978 | 6.48 |
| 50 | 0.584 | 3.87 |

USP = United States Pharmacopeia

EXAMPLE 5

As in Example 2 with a UK-containing solution.
Table 5 shows the result.

TABLE 5

| Concentrations of platelets added (cells/ml assay mixture) | $OD_{405\,nm}$ | Stimulation factor |
|---|---|---|
| 0 | 0.151 | 1.00 |
| 2.5 | 0.224 | 1.48 |
| 25 | 0.227 | 1.50 |
| 250 | 0.269 | 1.78 |
| 2500 | 0.459 | 3.04 |
| 25000 | 3.750 | 24.83 |
| 250000 | 0.385 | 2.55 |

EXAMPLE 6

As in Example 3 with a UK-containing solution.
Table 6 shows the results.

TABLE 6

| Concentrations of Staphylococci added (mg Staphylococci/ml assay mixture) | $OD_{405\,nm}$ | Stimulation factor |
|---|---|---|
| 0 | 0.151 | 1.00 |
| $10^{-4}$ | 0.151 | 1.00 |
| $10^{-3}$ | 0.151 | 1.00 |
| $10^{-2}$ | 0.180 | 1.19 |
| $10^{-1}$ | 0.204 | 1.35 |
| 1 | 1.018 | 6.74 |
| 10 | 0.394 | 2.61 |

I claim:

1. A method for the quantitative determination of a plasminogen activator (PA) from the group consisting of urokinase (UK) and tissue plasminogen activator (tPA) in body fluids, which comprises the steps of
incubating PA with plasminogen and with a polysulfuric ester of a saccharide or with a sulfated sugar under conditions effective to allow conversion of the plasminogen into plasmin; and
determining quantitatively the conversion of plasminogen into plasmin.

2. The method of claim 1, wherein said incubating step is further conducted in the presence of fibrin or fibrin degradation products.

3. The method of claim 2, wherein the determining step is further conducted with the use of a chromogenic substrate indicator.

4. The method as claimed in claim 3, wherein cell membrane constituents are used as the polysulfuric ester of a saccharide or as the sulfated sugar.

5. The method as claimed in claim 3, wherein the plasminogen activator is t-PA.

6. The method as claimed in claim 3, wherein the polysulfuric ester of a saccharide is heparin.

7. The method as claimed in claim 3, wherein heparin is used in a concentration of $10^{-8}$ to 1 mg/ml of assay mixture.

8. The method as claimed in claim 3, wherein the polysulfuric ester of a saccharide or the sulfated sugar is heparan sulfate, dermatan sulfate, chondroitin sulfate, pentosan sulfate, keratan sulfate or mucopolysaccharide polyslfate, in a concentration of $10^{-8}$ to 1 mg/ml in the assay mixture.

9. An agent for the quantitative determination of a plasminogen activator comprising at least from about 0.01 to about 1 CTA/ml plasminogen and from about $10^{-4}$ to 1 g/ml heparin.

10. The agent of claim 9 further comprising from about 0.01 to about 0.1 ml/100 ml polyoxyethylene sorbitan monooleate.

11. The agent of claim 10 further comprising fibrin degradation products.

* * * * *

UNITED STATES PATENT AND TRADEMARK OFFICE
CERTIFICATE OF CORRECTION

PATENT NO. : 4,818,690
DATED : April 4, 1989
INVENTOR(S) : Eric Paques

It is certified that error appears in the above-identified patent and that said Letters Patent is hereby corrected as shown below:

Claim 8, column 4, line 58, change "polyslfate" to --polysulfate--.

Signed and Sealed this

Ninth Day of October, 1990

Attest:

HARRY F. MANBECK, JR.

*Attesting Officer*  *Commissioner of Patents and Trademarks*